United States Patent [19]

Saygin

[11] 3,933,886

[45] Jan. 20, 1976

[54] DIAMINO-NITRO-BENZENE COMPOUNDS

[75] Inventor: Ferdi Saygin, Dusseldorf, Germany

[73] Assignee: Henkel & Cie GmbH, Dusseldorf, Germany

[22] Filed: May 16, 1974

[21] Appl. No.: 470,385

Related U.S. Application Data

[63] Continuation of Ser. No. 272,383, July 17, 1972, abandoned.

[30] Foreign Application Priority Data

Oct. 4, 1971 Germany............................ 2149467
Feb. 18, 1972 Germany............................ 2207683

[52] U.S. Cl.................... 260/465 D; 8/10.2; 8/32; 260/310 R; 260/332.2 A; 260/347.2; 260/471 A; 260/507 R; 260/518 A; 260/518 R; 260/558 P; 260/562 B; 260/562 K; 260/562 R

[51] Int. Cl.$^2$........................................ C07C 121/78
[58] Field of Search................... 260/465 D; 8/10.1

[56] References Cited

UNITED STATES PATENTS 3,634,478 1/1972 Halasz................................ 260/465

*Primary Examiner*—Lewis Gotts
*Assistant Examiner*—Dolph H. Torrence
*Attorney, Agent, or Firm*—Hammond & Littell

[57] ABSTRACT

A hair dye preparation contains diamino-nitrobenzene compounds as a direct hair dye or contains diamino-nitrobenzene compounds as coupling components in combination with developing components for oxidation dyestuffs. A process for dyeing human hair comprises applying one of these preparations to the hair.

3 Claims, No Drawings

DIAMINO-NITRO-BENZENE COMPOUNDS

This is a continuation, of Ser. No. 272,383, filed July 17, 1972 and now abandoned.

PRIOR ART

French Pat. No. 988,553 discloses the preparation of 1,4-diamino-2-nitro-benzene compounds per se, as well as those derivatives thereof having an acetoacetyl group substituted for one of the hydrogen atoms on the amino group nitrogen atom in the 4 position. French Pat. No. 988,579 discloses that 1,4-diamino-2-nitro-benzene compounds in which there is an acetoacetyl group substituted for one of the hydrogen atoms on the amino group nitrogen atom in the 4 position may be used as an intermediary for the synthesis of acidic azo dyes for textile fibers.

OBJECTS OF THE INVENTION

It is an object of the present invention to provide an aqueous hair dye preparation containing a diamino-nitro-benzene compound which acts as a direct dye or which acts as a coupling component along with a developer component in an oxidation dyestuffs combination.

It is another object of the present invention to provide a compound of the formulae selected from the group consisting of

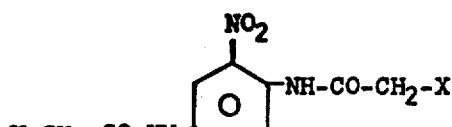

and

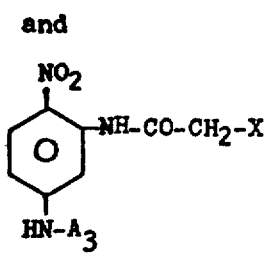

wherein X is an electrophilic substituent and $A_3$ is a member selected from the group consisting of alkyl of 1 to 10 carbon atoms, hydroxyalkyl of 1 to 10 carbon atoms, N,N-dialkyl-aminoalkyl of 3 to 18 carbon atoms, alkanoyl of 2 to 10 carbon atoms, substituted alkanoyl of 2 to 10 carbon atoms with a substituent selected from the group consisting of nitro, phenyl, halo, cyano, carboxyl and sulfo, acyl of aromatic hydrocarbon carboxylic acids having 7 to 15 carbon atoms, substituted acyl of aromatic hydrocarbon carboxylic acids having from 7 to 15 carbon atoms with a substituent selected from the group consisting of lower alkyl, nitro, halo, cyano, carboxyl and sulfo, and the activated methylene group —CO—CH$_2$—X, in which X is an electrophilic substituent.

It is a further object of the present invention to provide a process for dyeing human hair which comprises applying to the hair an aqueous hair dye preparation containing a diamino-nitrobenzene compound which acts as a direct dye or which acts as a coupling component along with a developer component in an oxidation dyestuffs combination.

Other and further objects of the present invention will become apparent as the description thereof proceeds.

DESCRIPTION OF THE INVENTION

The present invention provides a compound of the formulae selected from the group consisting of

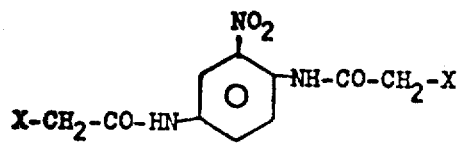

and

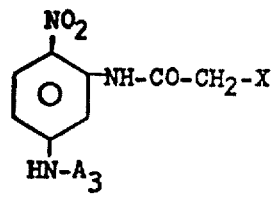

wherein X is an electrophilic substituent and $A_3$ is a member selected from the group consisting of alkyl of 1 to 10 carbon atoms, hydroxyalkyl of 1 to 10 carbon atoms, N,N-dialkyl-aminoalkyl of 3 to 18 carbon atoms, alkanoyl of 2 to 10 carbon atoms, substituted alkanoyl of 2 to 10 carbon atoms with a substituent selected from the group consisting of nitro, phenyl, halo, cyano, carboxyl and sulfo, acyl of aromatic hydrocarbon carboxylic acids having 7 to 15 carbon atoms, substituted acyl of aromatic hydrocarbon carboxylic acids having from 7 to 15 carbon atoms with a substituent selected from the group consisting of lower alkyl, nitro, halo, cyano, carboxyl and sulfo, and the activated methylene group —CO—CH$_2$—X, in which X is an electrophilic substituent.

The present invention also provides an aqueous preparation for the direct dyeing of human hair consisting essentially of (1) from 0.1% to 5% by weight of a diamino-nitrobenzene compound of the formula selected from the group consisting of

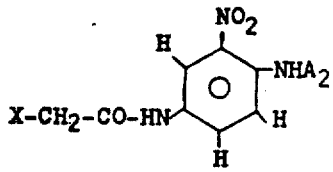

and

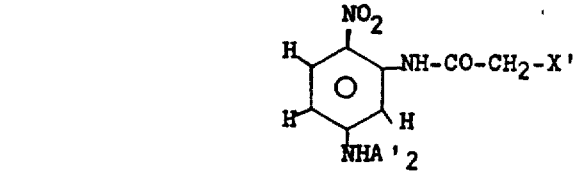

in which X and X' are each an electrophilic substituent and $A'_2$ is a member selected from the group consisting of hydrogen, alkyl of 1 to 10 carbon atoms, hydroxyalkyl of 1 to 10 carbon atoms, N,N-dialkyl-aminoalkyl of 3 to 18 carbon atoms, alkanoyl of 2 to 10 carbon atoms, substituted alkanoyl of 2 to 10 carbon atoms with a substituent selected from the group consisting of nitro, phenyl, halo, cyano, carboxyl and sulfo, acyl of aromatic hydrocarbon carboxylic acids having 7 to 15 carbon atoms, substituted acyl of aromatic hydrocarbon carboxylic acids having from 7 to 15 carbon atoms with a substituent selected from the group consisting of lower alkyl, nitro, halo, cyano, carboxyl and sulfo; and in which $A_2$ is selected from the group consisting of $A'_2$ and the activated methylene group $-CO-CH_2-X$, in which X is an electrophilic substituent with the proviso that whenever $A_2$ is hydrogen, then X is not acetyl; (2) from 0% to 30% by weight of a surfactant; (3) from 0% to 25% by weight of thickeners; and (4) from 40% to 99.9% by weight of water.

The present invention is further directed to a process for the direct dyeing of human hair consisting essentially of applying to said hair at temperatures ranging substantially from 15°C to 40°C for a time sufficient to affect dyeing, an effective amount of an aqueous preparation consisting essentially of (1) from 0.1% to 5% by weight of a diamino-nitrobenzene compound of the formula selected from the group consisting of

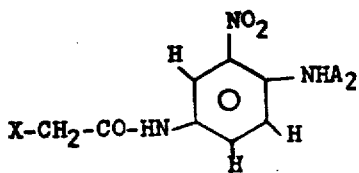

and

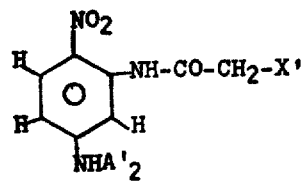

in which X and X' are each an electrophilic substituent and $A'_2$ is a member selected from the group consisting of hydrogen, alkyl of 1 to 10 carbon atoms, hydroxyalkyl of 1 to 10 carbon atoms, N,N-dialkyl-aminoalkyl of 3 to 18 carbon atoms, alkanoyl of 2 to 10 carbon atoms, substituted alkanoyl of 2 to 10 carbon atoms with a substituent selected from the group consisting of nitro, phenyl, halo, cyano, carboxyl and sulfo, acyl of aromatic hydrocarbon carboxylic acids having 7 to 15 carbon atoms, substituted acyl of aromatic hydrocarbon carboxylic acids having from 7 to 15 carbon atoms with a substituent selected from the group consisting of lower alkyl, nitro, halo, cyano, carboxyl and sulfo; and in which $A_2$ is selected from the group consisting of $A'_2$ and the activated methylene group $-CO-CH_2-X$, in which X is an electrophilic substituent; (2) from 0% to 30% by weight of a surfactant; (3) from 0% to 25% by weight of thickeners; and (4) from 40% to 99.9% by weight of water.

The present invention further provides an aqueous preparation for the dyeing of human hair consisting essentially of (1) from 0.1% to 5% by weight of an oxidation dyestuffs combination of a developer component, and a coupling component in substantially equimolar amounts, said coupling component consisting essentially of a diamino-nitrobenzene compound of the formula selected from the group consisting of

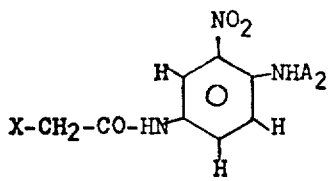

and

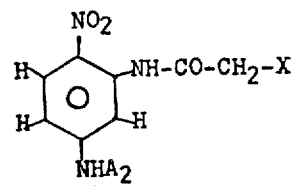

in which X is an electrophilic substituent and $A_2$ is a member selected from the group consisting of hydrogen, alkyl of 1 to 10 carbon atoms, hydroxyalkyl of 1 to 10 carbon atoms, N,N-dialkyl-aminoalkyl of 3 to 18 carbon atoms, alkanoyl of 2 to 10 carbon atoms, substituted alkanoyl of 2 to 10 carbon atoms with a substituent selected from the group consisting of nitro, phenyl, halo, cyano, carboxyl and sulfo, acyl of aromatic hydrocarbon carboxylic acids having 7 to 15 carbon atoms, substituted acyl of aromatic hydrocarbon carboxylic acids having from 7 to 15 carbon atoms with a substituent selected from the group consisting of lower alkyl, nitro, halo, cyano, carboxyl and sulfo, and the activated methylene group $-CO-CH_2-X$, in which X is an electrophilic substituent; (2) from 0% to 30% by weight of a surfactant; (3) from 0% to 25% by weight of thickeners; and (4) from 40% to 99.9% by weight of water.

The present invention is still further directed to a process for the dyeing of human hair consisting essentially of applying to said hair at temperatures ranging substantially from 15°C to 40°C for a time sufficient to affect dyeing, an effective amount of an aqueous preparation for the dyeing of human hair consisting essentially of (1) from 0.1% to 5% by weight of an oxidation dyestuffs combination of a developer component, and a coupling component in substantially equimolar amounts, said coupling component consisting essentially of a diamino-nitrobenzene compound of the formula selected from the group consisting of

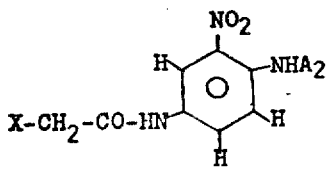

and

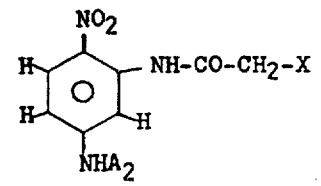

in which X is an electrophilic substituent and $A_2$ is a member selected from the group consisting of hydrogen, alkyl of 1 to 10 carbon atoms, hydroxyalkyl of 1 to 10 carbon atoms, N,N-dialkyl-aminoalkyl of 3 to 18 carbon atoms, alkanoyl of 2 to 10 carbon atoms, substituted alkanoyl of 2 to 10 carbon atoms with a substituent selected from the group consisting of nitro, phenyl, halo, cyano, carboxyl and sulfo, acyl of aromatic hydrocarbon carboxylic acids having 7 to 15 carbon atoms, substituted acyl of aromatic hydrocarbon carboxylic acids having from 7 to 15 carbon atoms with a substituent selected from the group consisting of lower alkyl, nitro, halo, cyano, carboxyl and sulfo, and the activated methylene group $—CO—CH_2—X$, in which X is an electrophilic substituent; (2) from 0% to 30% by weight of a surfactant; (3) from 0% to 25% by weight of thickeners; and (4) from 40% to 99.9% by weight of water.

As electrophilic substituents X, the radicals containing a carbonyl, such as carboxyl, alkoxycarbonyl, and acyl, or a nitrile, or carbonyl containing radicals further substituted with halogen, the sulfo group and the nitro group, are considered. X is preferably a nitrile, acyl, or alkoxycarbonyl group.

The acyl substituent can be derived from aliphatic, cycloaliphatic, heterocyclic or aromatic carboxylic acids and can themselves be substituted. Suitable examples of acyl groups include alkanoyl of 2 to 10 carbon atoms and their nitro, phenyl, halo, cyano, carboxyl and sulfo substituted derivatives, such as acetyl, butyryl, trifluoroacetyl, phenylacetyl, aromatic hydrocarbon carboxylic acids having 7 to 15 carbon atoms and their alkyl, nitro, halo, cyano, carboxyl and sulfo substituted derivatives, such as benzoyl, nitrobenzoyl, chlorobenzoyl, phthaloyl, β-naphthoyl, cycloalkylcarbonyl of 6 to 10 carbon atoms, such as cyclohexylcarbonyl, furoyl, and thenoyl. The alkoxycarbonyl groups represented by X may also be comprised by aromatic or cycloaliphatic radicals, usually alkyl of 1 to 10 carbon atoms; but also cycloalkyl of 6 to 10 carbon atoms and phenylalkyl of 7 to 16 carbon atoms; for example, they may be derived from benzyl alcohol or cyclohexyl alcohol.

For the reasons of greater availability of the starting material, it is preferable that the acyl substituent be derived from lower aliphatic carboxylic acids with 2 to 4 carbon atoms or from mononuclear aromatic carboxylic acids. The alkoxycarbonyl residues may be derived from lower aliphatic alcohols with 1 to 4 carbon atoms.

In addition to $A_2$ being the activated methylene group $—CO—CH_2—X$, $A_2$ could be any one of the above acyls or alkyl and hydroxyalkyl of 1 to 10 carbon atoms and N,N-dialkylaminoalkyl of 3 to 18 carbon atoms optionally present in the hair dyes of the invention may be present in an arbitrary manner. It is preferable, however, for the above named reasons, that they are short-chained. The alkyl or alkylol radicals preferably have 2 to 4 carbon atoms. The N,N-dialkylaminoalkyl residues are preferably derived from terminal alkyl amines of 2 to 12 carbon atoms, substituted by methyl and/or ethyl groups, for example dimethylaminopropyl, diethylaminohexyl, methylethylaminododecyl.

Of the compounds, falling under the general formula, the following are preferred:

1,3-diamino-4-nitrobenzene derivatives of the formula

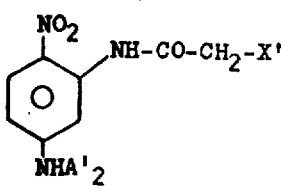

in which X' and $A'_2$ have the same meanings as defined above; and 1,4-diamino-nitrobenzene derivatives of the formula

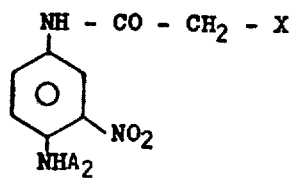

in which X has the same meaning as defined above and $A_2$ is a hydrogen atom or $—CO—CH_2—X$. Suitable examples for compounds of the above described subgeneric formulas are as follows: 1-amino-3-cyanoacetylamino-4-nitrobenzene, 1-benzoylacetylamino-3-amino-4-nitrobenzene, 1-methylamino-3-cyanoacetylamino-4-nitrobenzene, 1,3-di(cyanoacetylamino)-4-nitrobenzene, 1,3-Di-(ω-ethoxycarbonyl-acetylamino)-4-nitrobenzene, 1-Amino-3-(ω-ethoxycarbonyl-acetylamino)-4-nitrobenzene, 1-Acetylamino-3-cyanoacetylamino-4-nitrobenzene, 1-Amino-3-acetoacetylamino-4-nitro-benzene, 1-(p-Nitro-benzoylacetylamino)-3-amino-4-nitrobenzene, 1-Trifluoro-acetoacetylamino-3-amino-4-nitrobenzene, 1-(2-Hydroxy-ethylamino)-3-cyanoacetylamino-4-nitrobenzene, 1-Amino-2-nitro-4-ω-cyanoacetylamino-benzene, 1-Amino-2-nitro-4-ω-benzoyl-acetylamino-benzene, 1,4-Dicyanoacetylamino-2-nitrobenzene, 1-Amino-2-nitro-4-ω-ethoxycarbonylacetylamino-benzene, 1,4-Bis-(ω-ethoxycarbonyl-acetylamino)-2-nitrobenzene, 1-Amino-2-nitro-4-ω-benzoxycarbonyl-acetylamino-benzene, 1-Amino-2-nitro-4-(p-nitrobenzoyl-acetylamino)-benzene, 1-Amino-2-nitro-4-acetoacetylamino-benzene, 1-Amino-2-nitro-4-nitroacetoacetylamino-benzene, 1-Amino-2-nitro-4-trifluoroacetoacetylamino-benzene, 1-Amino-2-nitro-4-ω-butyryl-acetylamino-benzene, 1-Amino-2-nitro-4-ω-(β-Naphthoylacetylamino)-benzene, 1-Amino-2-nitro-4-eyclohexylcarbonyl-acetylamino-benzene, 1-Amino-2-nitro-4-Furoylacetylamino-benzene, 1-Amino-2-nitro-4-Thenoylacetylamino-benzene, 1,4-Bis-(ω-butoxycarbonyl-acetylamino)-benzene, 1,4-Bis-(ω-cyclohexyloxycarbonyl-acetylamino)-benzene.

The hair dyes of the present invention can be prepared by reacting a 1,3-diamino-4-nitrobenzene or a 1,4-diamino-nitrobenzene or their derivatives, substituted at an N-atom by the substituents named in the above formulas, with a suitably substituted acetyl chloride or acetic acid ester, such as with cyanoacetic acid ethyl ester or cyanoacetyl chloride, malonic acid dialkyl ester or malonic acid monoalkyl ester chloride, acetoacetic acid ethyl ester, benzoylacetic acid methyl ester or benzoylacetyl chloride.

The reaction of 1,3-diamino-4-nitrobenzene or 1,4-diaminonitrobenzene with substituted acetic acid esters, always results in derivatives having a mono substituted nitrogen, independent of the quantitative proportions of the reactants and the other reaction conditions.

The reaction to place a substituent on both amino groups takes place only if the reaction is carried out with substituted acetyl chloride in the presence of nonpolar solvents, such as benzene or hydrocarbons. However the reaction with substituted acetyl chloride in the presence of polar solvents, such as tetrahydrofuran or chlorobenzene, always results in derivatives, having one monosubstituted nitrogen independent of the quantitative proportions of the reactants.

In the case of the reaction with substituted acetic acid esters, the reaction may be carried out in the presence of solvents, whose polarity has no influence on the course of the reaction.

If acid chlorides are a reactant, it is preferable to add to the reaction mixture an acid acceptor, for example an amine, preferably a lower alkylamine or lower alkylolamine such as triethylamine.

The synthesis reaction is generally carried out at reflux temperatures, and in many cases can be followed by a progressive precipitation of the reaction product. The reaction time required is generally 3 to 5 hours. The reaction products may optionally be purified by recrystallization from polar solvents.

The hair dyes of the present invention may be used as direct dyes, with the exception of those derivatives of 1,3-diamino-4-nitrobenzene which are substituted on both amino groups by the methylene active grouping $-CO-CH_2-X$. In these direct dyes the member $A'_2$ excludes this methylene active grouping. All of these dyes are distinguished by their affinity to hair and by their ability to produce clear yellow dyeings of the hair.

A second important utility of the novel hair dyes is in their use as color coupling components for yellow-developers in oxidation hair dyes with conventional developers. The attainable shades can be varied by the developer components and the intensity of color produced by oxidation can be varied over a range of different tints from yellow to brown.

The hair dyes, according to the invention, are preferably used in about equal molar amounts with respect to the applied developers. However it is acceptable if the color coupling component is present in an amount greater than the equimolar quantity or less than the equimolar quantity.

Both the color coupling components and the developers may be mixtures of the respective compounds.

Examples of suitable developing agents include aromatic, bior polyfunctional amines having at least one primary amino group and another functional group in para-position, or else a 4-aminopyrazolone.

Preferred 4-aminopyrazolones are compounds of the generic formula (1)

$$R_3-C = C-NH_2 \atop HN \diagdown C=O \atop N \atop R_4$$ (1)

wherein $R_3$ and $R_4$ are hydrogen or an organic radical having 1 to 10 carbon atoms.

The organic radical $R_3$ can be an alkyl having 1 to 10 carbon atoms, an aryl, such as phenyl, hydroxyphenyl, sulfonylphenyl, sulfonamidophenyl, aminophenyl, lower alkylolphenyl, lower alkylphenyl, lower alkylaminophenyl and di-lower alkylaminophenyl where the alkyls and alkylols have 1 to 4 carbon atoms, or a heterocyclic radical, such as the pyridyl. Functional groups may be present, particularly on the aryl, as indicated above, such as OH, $NH_2$, $NHCH_3$, $N(CH_3)_2$ or halogen atoms, i.e., fluorine, iodine, bromine, and particularly chlorine. Furthermore, the following groups may be present as organic radicals: COCH, COOR', $CONH_2$, CONHR', CONR'R'', wherein R' and R'' are alkyl or hydroxyalkyl having 1 to 4 carbon atoms.

The organic radical $R_4$ can be an alkyl having 1 to 10 carbons, an aryl, such as those mentioned above for $R_3$, or a heterocyclic radical, such as the pyridyl. Functional groups may be present. Particularly, hydrocarbon radicals having 1 to 10 carbons are applicable containing as functional groups OH, $NH_2$, COOH, $CONH_2$, $SO_3H$ and $SO_2NH_2$.

As aromatic radical, a phenyl is especially applicable. It may be substituted with alkyl or hydroxyalkyl groups having 1 to 4 carbons or other substituents, such as halogen, preferably Cl, $NH_2$, OH, COOH, $CONH_2$, CONHR', CONHR'R'', $SO_3H$ and $SO_2NH_2$.

It frequently is opportune to employ the 4-aminopyrazolones in the form of their water-soluble acid addition salts, such as the hydrochloride, sulfate or oxalate, because the resistance to atmospheric air is increased.

4-Aminopyrazolones which are suitable in the process of the invention as formula (1) are as follows:

1-ethyl-4-aminopyrazolone
1-n-hexyl-4-aminopyrazolone
1-n-decyl-4-aminopyrazolone
1-phenyl-4-aminopyrazolone
1-(p-hydroxyphenyl)-4-aminopyrazolone
1-(p-sulfonylphenyl)-4-aminopyrazolone
3-methyl-4-aminopyrazolone
3-i-propyl-4-aminopyrazolone
3-n-octyl-4-aminopyrazolone
3-phenyl-4-aminopyrazolone
3-(p-ethylphenyl)-4-aminopyrazolone
3-(p-aminophenyl)-4-aminopyrazolone
3-(p-dimethylaminophenyl)-4-aminopyrazolone
3-(m-chlorophenyl)-4-aminopyrazolone
3-(4-pyridyl)-4-aminopyrazolone
1-methyl-3-phenyl-4-aminopyrazolone
1-ethyl-3-(o-hydroxyphenyl)-4-aminopyrazolone
1-n-decyl-3-(p-methylaminophenyl)-4-aminopyrazolone
1-phenyl-3-n-butyl-4-aminopyrazolone
1-(p-sulfonamidophenyl)-3-n-octyl-4-aminopyrazolone
1-(p-sulfonamidophenyl)-3-phenyl-4-aminopyrazolone
1-(p-ethylphenyl)-3-phenyl-4-aminopyrazolone
1-(p-beta-hydroxyethylphenyl)-3-phenyl-4-aminopyrazolone
1-(p-hydroxyphenyl)-3-n-octyl-4-aminopyrazolone
1-(p-carboxyphenyl)-3-n-octyl-4-aminopyrazolone
1-(p-carbamidophenyl)-3-n-octyl-4-aminopyrazolone
4-aminopyrazolone-3-carboxylic acid
4-aminopyrazolone-3-carboxylic acid-ethyl ester
4-aminopyrazolone-3-carboxylic acid-n-butyl ester
4-aminopyrazolone-3-carboxylic acid-methylamide
4-aminopyrazolone-3-carboxylic acid-hydroxymethylamide 4-aminopyrazolone-3-carboxylic acid-di-n-butylamide
4-aminopyrazolone-3-carboxylic acid-ethyl-beta-hydroxyethylamide
1-methyl-4-aminopyrazolone-3-carboxylic acid-ethyl ester
1-methyl-4-aminopyrazolone-3-carboxylic acid-n-propylamide
1-methyl-4-aminopyrazolone-3-carboxylic acid-beta-hydroxypropylamide
1-ethyl-4-aminopyrazolone-3-carboxylic acid-methyl ester
1-ethyl-4-aminopyrazolone-3-carboxylic acid-amide
1-n-propyl-4-aminopyrazolone-3-carboxylic acid-beta-hydroxybutylamide
1-i-propyl-4-aminopyrazolone-3-carboxylic acid-beta-hydroxyethylamide
1-n-butyl-4-aminopyrazolone-3-carboxylic acid-methyl ester
1-n-hexyl-4-aminopyrazolone-3-carboxylic acid-ethyl ester
1-n-heptyl-4-aminopyrazolone-3-carboxylic acid
1-n-decyl-4-aminopyrazolone-3-carboxylic acid-di-n-propylamide
1-n-decyl-4-aminopyrazolone-3-carboxylic acid-beta-hydroxyethyl ester
1-phenyl-4-aminopyrazolone-3-carboxylic acid
1-phenyl-4-aminopyrazolone-3-carboxylic acid-ethyl ester
1-phenyl-4-aminopyrazolone-3-carboxylic acid-$\beta$-hydroxyethyl ester
1-phenyl-4-aminopyrazolone-3-carboxylic acid-amide
1-phenyl-4-aminopyrazolone-3-carboxylic acid-ethylamide
1-phenyl-4-aminopyrazolone-3-carboxylic acid-beta-hydroxyethylamide
1-phenyl-4-aminopyrazolone-3-carboxylic acid-dimethylamide
1-(p-i-propylphenyl)-4-aminopyrazolone-3-carboxylic acid
1-(p-hydroxyphenyl)-4-aminopyrazolone-3-carboxylic acid-ethyl ester
1-(p-aminophenyl)-4-aminopyrazolone-3-carboxylic acid-amide
1-(o-carboxyphenyl)-4-aminopyrazolone-3-carboxylic acid-ethyl ester
1-(p-sulfonylphenyl)-4-aminopyrazolone-3-carboxylic acid-ethyl ester
1-(p-sulfonamidophenyl)-4-aminopyrazolone-3-carboxylic-acid-ethyl ester
1-(2-pyridyl)-4-aminopyrazolone-3-carboxylic acid-diethylamide These compounds may be used as such or in the form of their water-soluble acid addition salts.

Suitable aromatic bi- and polyfunctional amines having at least one primary amino group and another functional group in para-position are, e.g., p-phenylenediamine, p-toluylenediamine, p-diaminoanisole, p-aminomethylaniline, p-aminoethylaniline, p-aminodiphenylamine, p-aminodimethylaniline, p-aminodiethylaniline, p-amino-di-beta-hydroxyethylaniline, p-aminophenyl, p-diaminoanisole, or compounds of the kind named which additionally contain one or more functional groups such as OH, NH$_2$, NHR', NR'R'', wherein R' and R'' again are lower alkyls or hydroxyalkyls having 1 to 4 carbon atoms.

Preferably, these aromatic bi- and polyfunctional amines have the formula

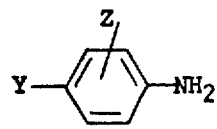

wherein Y is a member selected from the group consisting of OH, NH$_2$, NHR', NR'R'' and NHC$_6$H$_5$ and Z is a member selected from the group consisting of H, R', Y and OR', where again R' and R'' are alkyls or hydroxyalkyls having 1 to 4 carbon atoms.

These aromatic bi- or polyfunctional amines advantageously are employed in substantially equimolar amounts, calculated on the pyrazolones substituted in the 3-position. However, it is not disadvantageous to apply these pyrazolones in a given excess or in amounts slightly less than molar. Mixtures of the individual dyestuff components can be used.

Dyeing of the hair is carried out in aqueous media and, as customary for oxidation dyes, developed either by the action of atmospheric oxygen or by means of chemical oxidizers, preferably hydrogen peroxide or its adducts on urea, melamine, or sodium borate and mixtures of such hydrogen peroxide adducts with potassium peroxydisulfate. Effective temperatures are substantially 15° to 40°C, preferably room temperature.

The hair dyes of the invention can be present in the above named uses in the form of aqueous preparations, such as solutions or emulsions. Such solutions should contain the dyes or the dye combinations of coupling- and developing components in amounts from 0.1 to 5%, particularly 2% by weight.

The compounds of the invention may also be applied in the form of creams or emulsions. To make such creams or emulsions, any desired surfactants may be employed, but especially anionic or non-ionic detergents or wetting agents. Suitable surfactants are particularly alkylbenzenesulfonates, higher fatty alcohol sulfates, higher alkylsulfonates, higher fatty acid ethanolamides, ethylene oxide adducts on higher fatty acids, higher fatty alcohols or alkylphenols.

The dyeability of the materials named is not diminished in the presence of the surfactants or, in other words, when applied in cream form. Thus, the dyeing agents according to the invention can be manufactured in the form of shampoos, particularly cream shampoos, as frequently is desired in practice.

Moreover, other agents can be incorporated into the agents, such as thickeners in the form of methyl or hydroxymethyl-cellulose, starch, higher fatty alcohols, "Vaseline," paraffin oils and higher fatty acids. Perfumes, i.e., essential oils, or hair grooming agents such as pantothenic acid and cholesterol, also may be incorporated.

Effective amounts of the additives names above are those customarily employed. Effective amounts for surfactants range from 0.5 to 30%, for thickeners from 0.1 to 25%, and the effective concentration of the dyestuffs or dyestuffs combination depending upon the use, range from 0.1% to 5% by weight, preferably 0.1% to 2% by weight. All these percentages are by weight and calculated on the total composition.

The hair dyes can be applied to the hair in weakly acid, neutral and preferably alkaline pH ranges at temperatures of from 15°C to 40°C.

The dyeings attained are distinguished by good light and wash fastness and fastness to rubbing. A new and unexpected advantage and a surprising property of the hair dye solutions and process, according to the invention, is that the hair dye solutions may be applied both as direct dyes and as coupling dyestuff agents in oxidation dyes for the ointment of yellow and blond hair dyeings.

The following examples are merely illustrative of the present invention without being deemed limitative in any manner thereof.

EXAMPLE I

1-Amino-3-cyanoacetylamino-4-nitrobenzene 9.04 gm (0.059 mol) of 1,3-diamino-4-nitrobenzene, 5.69 gm (0.054 mol) of cyanoacetyl chloride were boiled in 100 ml of benzene for 4 hours at reflux. The precipitation of the reaction product occurred during the reaction and was completed by concentration of the reaction solution. The separated precipitate was purified by recrystallization from acetic acid. On the basis of the analysis data and IR- and NRM-measurements the product has the formula: 1-amino-3-cyanoacetylamino-4-nitrobenzene and a melting point of 218°–220°C.

| Analysis: | C | H | N |
|---|---|---|---|
| Calculated: | 49.09% | 3.66% | 25.46% |
| Found: | 48.80% | 3.63% | 25.13% |

EXAMPLES II – VII

In an analogous manner, the compounds listed in Examples 2 to 6 of the following table were obtained by reaction of 1,3-diamino-4-nitrobenzene with the following named compounds, while in Example 7 the starting materials were 1-acetylamino-3-amino-4-nitrobenzene and cyanoacetyl chloride.

lized from dilute acetic acid. The product has a melting point of 232°–233°C.

| Analysis: ($C_{12}H_9N_5O_4$) | C | H | N |
|---|---|---|---|
| Calculated: | 50.17% | 3.14% | 24.39% |
| Found: | 49.99% | 2.98% | 24.40% |

EXAMPLE IX

1-Amino-2-nitro-4-ω-cyanoacetylamino-benzene 15.3 gm (0.1 mol) of 1,4-diamino-2-nitrobenzene were heated to boiling in 150 ml of ethyl cyanoacetate. Simultaneously therewith the ethanol formed during the reaction was removed by distillation. After the reaction mixture was cooled, the precipitate formed was vacuum filtered, washed with ether and recrystallized from dilute acetic acid. The product had a melting point of 218°–221°C.

| Analysis: ($C_9H_8N_4O_3$) | C | H | N |
|---|---|---|---|
| Calculated: | 49.09% | 3.64% | 25.45% |
| Found: | 49.20% | 3.48% | 25.47% |

EXAMPLE X

1-Amino-2-nitro-4-ω-benzoylacetylamino-benzene 15.3 gm (0.1 mol) of 1,4-diamino-2-nitrobenzene were suspended in 100 ml of xylol. This suspension was heated. After the addition thereto of 42.3 gm (0.22 mol) of ethyl benzoylacetate, this suspension was heated on an oil bath at 130°C with the simultaneous distillation of ethanol, formed in the reaction. The precipitate was separated from the cold reaction mixture and processed, as described in Example I. The product had a melting point of 182°–183°C.

TABLE I

| Example No. | Reaction-Partner | Reactions-Product | Molar Ratio | Analysis % Calc = Calculated | | | | M.P. °C |
|---|---|---|---|---|---|---|---|---|
| | | | | | C | H | N | |
| 2 | Benzoyl-acetic acid ethyl ester | 3-Benzoylacetylamino-1-amino-4-nitrobenzene | 1 : 1 | Calc. Found | 60.20 60.19 | 4.38 4.55 | 14.04 14.03 | 219–221 |
| 3 | Cyanoacetyl-chloride | 1,3-Di(cyanoacetyl-amino)-4-nitrobenzene | 2 : 1 | Calc. Found | 50.18 50.13 | 3.16 2.79 | 24.38 25.35 | 223–226 |
| 4 | Malonic acid mono-ethyl ester chloride | 1,3-Di-(ω-ethoxycar-bonyl-acetylamino)-4-nitrobenzene | 2 : 1 | Calc. Found | 50.39 50.46 | 5.02 4.30 | 11.01 10.94 | 94–96 |
| 5 | Malonic acid mono-ethyl ester chloride | 1-Amino-3-(ω-ethoxy-(*) carbonyl-acetylamino)-4-nitrobenzene | 1 : 1 | Calc. Found | 49.43 48.43 | 4.90 4.61 | 15.73 15.83 | 172–173 |
| 6 | Acetoacetic acid ethyl ester | 1-Amino-3-acetoacetyl-amino-4-nitrobenzene | 1 : 1 | Calc. Found | 50.65 50.63 | 4.67 4.61 | 17.71 17.67 | 139–140 |
| 7 | Cyanoacetyl-chloride | 1-Acetylamino-3-cyano-acetylamino-4-nitro-benzene | 1 : 1 | Calc. Found | 50.38 50.39 | 3.84 3.72 | 21.37 22.56 | 232–235 |

(*)in the presence of an equimolar amount of triethylamine

EXAMPLE VIII 1,4-Dicyanoacetylamino-2-nitrobenzene 20.70 gm (0.2 mol) of cyanoacetyl chloride were dissolved in 370 ml of absolute benzene. 15.3 gm (0.1 mol) of 1,4-diamino-2-nitrobenzene were added to this solution, and the reaction mixture was heated for 6 hours at boiling. After cooling, the precipitate formed was vacuum filtered, washed with ether and recrystal-

| Analysis: ($C_{15}H_{13}N_3O_4$) | C | H | N |
|---|---|---|---|
| Calculated: | 60.20% | 4.35% | 14.05% |
| Found: | 59.41% | 3.84% | 14.09% |

EXAMPLE XI

1-Amino-2-nitro-4-(ω-ethoxycarbonyl-acetylamino)-benzene 7.65 gm (0.05 mol) of 1,4-diamino-2-nitrobenzene were added to 80 ml of absolute tetrahydrofuran and 5.1 gm (0.05 mol) of triethylamine at room temperature to form a solution. While this mixture was being stirred, 7.5 gm (0.05 mol) of malonic acid monoethylester chloride were added dropwise thereto. After termination of the addition, the mixture was stirred at room temperature for another 6 hours. Then the solvent was evaporated in vacuo for the most part. The residue was suctioned off and recrystallized once from ethanol/activated charcoal and a second time from water. The product had a melting point of 133°–136°C.

| Analysis: ($C_{11}H_{13}N_3O_5$) | C | H | N |
|---|---|---|---|
| Calculated: | 49.44% | 4.87% | 15.73% |
| Found: | 49.99% | 4.67% | 15.38% |

EXAMPLE XII 1,4-Bis-(ω-ethoxycarbonyl-acetylamino)-2-nitrobenzene 15.3 gm (0.1 mol) of 1,4-diamino-2-nitrobenzene were heated in 160 ml of absolute benzene together with 30.1 gm (0.2 mol) of malonic acid monoethylester chloride for 3½ hours at refluxing. After cooling the precipitate was suctioned off and recrystallized twice from isopropanol. The product had a melting point of 96°–97°C.

| Analysis: ($C_{16}H_{19}N_3O_8$) | C | H | N |
|---|---|---|---|
| Calculated: | 50.39% | 4.99% | 11.02% |
| Found: | 49.94% | 5.16% | 11.06% |

EXAMPLE XIII

1-Amino-2-nitro-4-acetoacetylamino-benzene 15.3 gm (0.1 mol) of 1,4-diamino-2-nitrobenzene were heated in 50 ml of chlorobenzene together with 20 gm of acetoacetic acid ethyl ester, with the simultaneous distillation of ethanol, formed in the reaction. From the cold reaction mixture the precipitate was suctioned off, washed with dilute methanol and recrystallized from dilute acetic acid. The product had a melting point of 146°–147°C.

| Analysis: ($C_{10}H_{11}N_3O_4$) | C | H | N |
|---|---|---|---|
| Calculated: | 56.65% | 4.67% | 17.71% |
| Found: | 56.65% | 4.29% | 17.73% |

EXAMPLE XIV

Into a cream emulsion of the following composition:
10 parts by weight of fatty alcohols $C_{16}$–$C_{18}$
10 parts by weight of fatty alcohol sulfate (technical mixture $C_{16}$–$C_{18}$)
75 parts by weight of water,
were incorporated
2 parts by weight of 1-amino-2-nitro-4-(ω-cyanoacetylamino)-benzene
and the pH of the mixture adjusted to 9.5 by the addition of ammonia. Enough water was added to bring the emulsion up to 100 parts by weight total. The thusly obtained dye cream dyed natural-16 greyed hair within 30 minutes to a buttercup yellow color. With dye creams of the same composition, which contained instead of the above named dye, the below listed compounds, the following hair colors could be obtained:

| Dye Component | Color Produced |
|---|---|
| 1,4-dicyanoacetylamino-2-nitrobenzene | corn yellow |
| 1-amino-2-nitro-4-(ω-benzoylacetylamino)-benzene | light yellow |
| 1-amino-2-nitro-4-(ω-ethoxycarbonyl-acetylamino)-benzene | yellow |
| 1-amino-2-nitro-4-acetoacetylamino-benzene | yellow-orange |
| 1-amino-3-(ω-cyanoacetylamino)-4-nitrobenzene | intensive maize |
| 1-amino-3-(ω-benzoylacetylamino)-4-nitrobenzene | mimosa yellow |
| 1-amino-3-(ω-ethoxycarbonylacetylamino)-4-nitro-benzene | pale yellow |
| 1-amino-3-(ω-acetoacetylamino)-4-nitrobenzene | primrose yellow |
| 1-acetylamino-3-(ω-cyanoacetylamino)-4-nitro-benzene | greenish-yellow |

EXAMPLES XV to XIX

2% aqueous solutions of oxidation dye combinations were prepared from equimolar amounts of a coupling component taken from the examples listed below together with 4-amino-1-phenyl-3-carbamoyl-pyrazolone-5 as the developer component. The pH of each solution was adjusted to 9.5 by the addition of ammonia. Then after mixing each solution with the same volume of a 1% or of a 9% hydrogen peroxide solution, samples of natural greyed hair were treated with the dye solution. The treatment took place at room temperature (22°C). The colors produced by the hair dyeing solutions are summarized in the following Table II.

TABLE II

| Example No. | Substance according to Example No. | 1% $H_2O_2$ | Color Produced 9% $H_2O_2$ |
|---|---|---|---|
| 15 | 1 | brownish yellow | nankeen yellow |
| 16 | 2 | golden yellow | chick yellow |
| 17 | 3 | red orange | yellow orange |
| 18 | 5 | brownish yellow | Genista yellow |
| 19 | 7 | golden yellow | buttercup yellow |

EXAMPLES XX to XXXI

Into a cream emulsion of the following composition:
10 parts by weight of fatty alcohols of the chain length $C_{12} - C_{18}$
10 parts by weight of fatty alcohol sulfate (Na salt) of the same chain length, and
75 parts by weight of water, were incorporated
0.01 mol of the below named coupling component and developer component. The pH of the emulsion was adjusted to 9.5 by the addition of ammonia. Enough water was added to bring the emulsion up to 100 parts by weight total. Added to the emulsion was an equal volume of an oxidizing agent comprising a 1% or a 9% by weight solution of hydrogen peroxide. This mixture was applied to naturally grey hair for 30 minutes. The respective color produced from the various oxidation dyestuff combinations of coupler component and developer component are listed in Table III below.

10 parts by weight of fatty alcohols of the chain length $C_{12} - C_{18}$ 10 parts by weight of fatty alcohol sulfate (Na salt) of the same chain length, and 75 parts by weight of water, were incorporated 0.01 mol of the below named coupling component and developer component. The pH of the emulsion was adjusted to 9.5 by the addition of ammonia. Enough water was added to bring the emulsion up to 100 parts by weight total. Added to the emulsion was an equal volume of a chemical oxidizing agent comprising a 1% or a 9% by weight solution of hydrogen peroxide. This mixture was applied to naturally grey hair for 30 minutes. If instead of adding a hydrogen peroxide solution, air were used as the oxidizing agent, the treatment time would be 30 minutes. The respective color produced

TABLE III

| Example No. | Dye Components Coupler | Developer | Color 1% $H_2O_2$ | 9% $H_2O_2$ |
|---|---|---|---|---|
| 20 | 1-amino-3-cyanoacetyl-amino-4-nitrobenzene | 2,5-diamino-anisole | olive brown | olive yellow |
| 21 | " | N,N-dimethylamino-aniline | " | " |
| 22 | " | p-toluylenediamine | coffee brown | coffee brown |
| 23 | " | 1-phenyl-3-methyl 1,3,4-thiadiazole-hydrazone-5 | canary yellow | canary yellow* |
| 24 | " | 1-ethyl-pyridone-2-hydrazone | moss green | moss green* |
| 25 | 1-acetylamino-3-cyano-acetylamino-4-nitrobenzene | p-toluylenediamine | olive green | honey yellow |
| 26 | 1-benzoylacetylamino-3-amino-4-nitrobenzene | p-toluylenediamine | olive brown | olive yellow |
| 27 | 1,3-di(ω-ethoxycarbonyl-acetylamino)-4-nitrobenzene | p-toluylenediamine | grey brown | grey brown |
| 28 | 1-amino-3-(ω-ethoxycarbonyl-acetylamino)-4-nitrobenzene | p-toluylenediamine | grey brown | olive brown |
| 29 | " | N,N-dimethylamino-aniline | dark green | gray-green |
| 30 | " | 4-amino-1-phenyl-3-ethoxycarbonyl-pyrazolone-5 | golden yellow | lemon yellow |
| 31 | " | 1-methyl-pyridone-2-hydrazone | grey-green | grey-green* |

*4% $H_2O_2$

EXAMPLES XXXII - L

Into a cream emulsion of the following composition:

from the various oxidation dyestuff combinations of coupler component and developer component are listed in the table below.

TABLE IV

| Example | Dye Components a) developer | b) coupling agent | Shade of dyed hair by air oxidation | 1% $H_2O_2$ solution | 9% $H_2O_2$ solution |
|---|---|---|---|---|---|
| 32 | 4-amino-1-phenyl-3-carbamoyl-pyrazolone-5 | 1-amino-2-nitro-4-cyanoacetylamino-benzene | brown yellow | brown orange | yellow orange |
| 33 | p-toluylenediamine | " | banana yellow | dark brown | oak brown |
| 34 | N-methyl-pyridone-2-hydrazone | " | cream colored | olive brown | purple grey* |
| 35 | 4-amino-1-phenyl-3-carbamoyl-pyrazolone-5 | 1,4-bis-cyanoacetyl-amino-2-nitro-benzene | pompeian red | brown orange | apricot yellow |
| 36 | p-toluylenediamine | " | apricot yellow | reddish brown | camel brown |
| 37 | N-methyl-pyridone-2-hydrazone | " | mustard yellow | olive | — |
| 38 | 4-amino-1-phenyl-3- | 1-amino-2-nitro-4- | apricot yellow | caramel brown | apricot brown |

TABLE IV-continued

| Example | Dye Components a) developer | b) coupling agent | Shade of dyed hair by air oxidation | 1% H₂O₂ solution | 9% H₂O₂ solution |
|---|---|---|---|---|---|
| 39 | carbamoyl-pyrazolone-5 4-amino-1-phenyl-3-ethoxycarbonyl-pyrazolone-5 | ω-ethoxycarbonyl-acetylaminobenzene " | apricot yellow | apricot yellow | bright brown orange |
| 40 | p-toluylenediamine | 1-amino-2-nitro-4-ω-ethoxycarbonyl-acetylaminobenzene | ocher yellow | light brown | cocoa brown |
| 41 | N,N-dimethylamino aniline | " | ocher yellow | brown | brown |
| 42 | N-methyl-pyridone-2-hydrazone | " | clay yellow | light brown | madeira brown* |
| 43 | 4-amino-1-phenyl-3-N-(β-hydroxyethyl-carbamoyl)-pyrazolone-5 | 1-amino-2-nitro-4-ω-ethoxycarbonyl-acetyl-amino-benzene | brass colored | ocher yellow | ocher yellow |
| 44 | 4-amino-3-ethoxy-carbonyl-1-H-pyrazolone-5 | 1-amino-2-nitro-4-ethoxycarbonyl-acetylamino-benzene | pompeian yellow | autumn-golden | deep yellow |
| 45 | 4-amino-1-phenyl-3-carbamoyl-pyrazolone-5 | 1-amino-2-nitro-4-acetoacetylaminobenzene | golden yellow | yellowish-brown | light brown |
| 46 | p-toluylenediamine | " | orange brown | brownish yellow | yellowish brown |
| 47 | N-methyl-pyridone-2-hydrazone | 1-amino-2-nitro-4-acetoacetylaminobenzene | golden yellow | golden yellow | — |
| 48 | 4-amino-1-phenyl-3-carbamoyl-pyrazolone-5 | 1-amino-2-nitro-4-benzoylacetylaminobenzene | caramel brown | reddish golden | light orange |
| 49 | p-toluylenediamine | " | caramel brown | dark brown | light brown |
| 50 | N-methyl-pyridone-2-hydrazone | " | olive yellow | — | — |

*4% H₂O₂-solution

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

I claim:

1. A compound of the formulae selected from the group consisting of

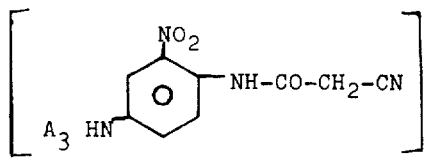

and

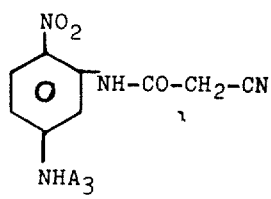

wherein $A_3$ is a member selected from the group consisting of hydrogen, alkyl of 1 to 4 carbon atoms, hydroxyalkyl of 1 to 4 carbon atoms, alkanoyl of 2 to 10 carbon atoms, cyano alkanoyl of 2 to 10 carbon atoms in the alkanoyl and acyl of aromatic hydrocarbon carboxylic acids having 7 to 15 carbon atoms.

2. A compound of the formulae selected from the group consisting of

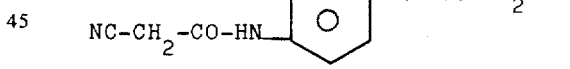

and

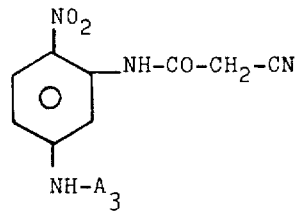

wherein $A_3$ is a member selected from the group consisting of alklyl of 1 to 10 carbon atoms, hydroxyalkyl of 1 to 10 carbon atoms, alkanoyl of 2 to 10 carbon atoms, and the activated methylene group —CO—CH₂—CN.

3. A compound according to claim 2, which is 1-acetylamino-3-cyanoacetylamino-4-nitro-benzene.

UNITED STATES PATENT OFFICE
CERTIFICATE OF CORRECTION

Patent No. 3,933,886  Dated January 20, 1976

Inventor(s) Ferdi Saygin

It is certified that error appears in the above-identified patent and that said Letters Patent are hereby corrected as shown below:

Column 4, line 24, "N,Ndialkyl-aminoalkyl" should read

-- N,N-dialkyl-aminoalkyl --.

Column 7, line 50, "bior" should read -- bi- or --.

Column 8, line 8, "COCH" should read -- COOH --.

Column 11, line 7, "ointment" should read -- obtainment --.

Column 17, lines 45-50, Claim 1, cancel the formula.

Column 17, line 59, cancel the underlining .

Signed and Sealed this

Thirtieth Day of November 1976

[SEAL]

Attest:

RUTH C. MASON
*Attesting Officer*

C. MARSHALL DANN
*Commissioner of Patents and Trademarks*